(12) United States Patent
Shipp et al.

(10) Patent No.: US 7,207,997 B2
(45) Date of Patent: Apr. 24, 2007

(54) LIGATION CLIP AND CLIP APPLIER

(76) Inventors: John I. Shipp, 329 W. Lincoln St., Tullahoma, TN (US) 37388; Steven Y. Shepard, 2621 Bransford Trail, Owens Crossroads, AL (US) 35763; James A. Satterfield, 2707 Whistler La., Hampton Cove, AL (US) 35273

( * ) Notice: Subject to any disclaimer, the term of this patent is extended or adjusted under 35 U.S.C. 154(b) by 343 days.

(21) Appl. No.: 10/721,681

(22) Filed: Nov. 25, 2003

(65) Prior Publication Data

US 2004/0106936 A1    Jun. 3, 2004

Related U.S. Application Data

(60) Continuation of application No. 10/082,915, filed on Feb. 25, 2002, now Pat. No. 6,652,545, which is a division of application No. 09/258,943, filed on Mar. 1, 1999, now Pat. No. 6,350,269.

(51) Int. Cl.
*A61C 17/12* (2006.01)
*A61B 17/122* (2006.01)
*A61B 17/10* (2006.01)

(52) U.S. Cl. ............... 606/157; 606/155; 606/143

(58) Field of Classification Search ........... 606/151, 606/155, 157, 158, 120; 132/64.1, 276–280, 132/283, 284
See application file for complete search history.

(56) References Cited

U.S. PATENT DOCUMENTS 648,841 A   5/1900   Brosnan
1,458,797 A   6/1923   Beale
2,498,372 A * 2/1950   Kortlucke, Jr. et al. ..... 606/120
2,626,608 A   1/1953   Garland (Continued)

FOREIGN PATENT DOCUMENTS

CA           2143560        2/1995

(Continued)

*Primary Examiner*—Cary E. O'Connor
(74) *Attorney, Agent, or Firm*—Martin & Ferraro, LLP

(57) ABSTRACT

The ligation clip applicator and ligation clip design are provided which are particularly applicable to placement of a surgical ligation clip during a laparoscopic surgical procedure. The clip includes a support member and a clamping arm having enlarged portions thereon. The applicator device has a magazine including first and second longitudinally extending partially closed channels within which the enlarged portions of the support member and the clamping arm are received with the clip held in an open position. First and second articulated jaws are attached to the magazine and have first and second channel extensions therein aligned with the first and second channels of the magazine, so that a clip can be received from the magazine in the jaws with the first and second enlarged portions of the support member and the clamping arm being received in the first and second channel extensions of the jaws. The channel extensions include first and second releasing openings. The jaws are closed about a vessel to pre-clamp the vessel. The clip is pushed forward into the jaws to a position where the enlarged portions of the support member and the clamping arm are aligned with the releasing openings and the support member and the clamping arm are released allowing the support member and the clamping arm to move toward each other to ligate the vessel therebetween.

12 Claims, 11 Drawing Sheets

U.S. PATENT DOCUMENTS

| | | |
|---|---|---|
| 2,874,384 A | 2/1959 | Krone |
| 2,876,778 A | 3/1959 | Kees, Jr. |
| 3,023,039 A | 2/1962 | Henningsen et al. |
| 3,023,468 A | 3/1962 | Hord et al. |
| 3,032,039 A | 5/1962 | Beaty |
| 3,056,408 A | 10/1962 | Brown |
| 3,098,232 A | 7/1963 | Brown |
| 3,120,230 A | 2/1964 | Skold |
| 3,274,658 A | 9/1966 | Pile |
| 3,363,628 A | 1/1968 | Wood |
| 3,439,523 A | 4/1969 | Wood |
| 3,476,114 A | 11/1969 | Shannon et al. |
| 3,518,993 A | 7/1970 | Blake |
| 3,631,707 A | 1/1972 | Miller |
| 3,675,688 A | 7/1972 | Bryan et al. |
| 3,757,629 A | 9/1973 | Schneider |
| 3,777,538 A | 12/1973 | Weatherly et al. |
| 3,827,277 A | 8/1974 | Weston |
| 3,827,438 A | 8/1974 | Kees, Jr. |
| 3,882,854 A | 5/1975 | Hulka et al. |
| 3,911,923 A | 10/1975 | Yoon |
| 3,955,581 A | 5/1976 | Spasiano et al. |
| 3,989,049 A | 11/1976 | Yoon |
| 4,017,337 A | 4/1977 | Winter et al. |
| 4,024,868 A | 5/1977 | Williams |
| 4,027,510 A | 6/1977 | Hiltebrandt |
| 4,038,987 A | 8/1977 | Komiya |
| 4,041,931 A * | 8/1977 | Elliott et al. ................. 128/899 |
| 4,064,881 A | 12/1977 | Meredith |
| 4,086,926 A | 5/1978 | Green et al. |
| 4,152,920 A | 5/1979 | Green |
| 4,169,476 A | 10/1979 | Hiltebrandt |
| 4,170,990 A | 10/1979 | Baumgart et al. |
| 4,196,836 A | 4/1980 | Becht |
| 4,217,902 A | 8/1980 | March |
| 4,226,239 A | 10/1980 | Polk et al. |
| 4,226,242 A | 10/1980 | Jarvik |
| 4,228,895 A | 10/1980 | Larkin |
| 4,241,734 A | 12/1980 | Kandel et al. |
| 4,242,902 A | 1/1981 | Green |
| 4,246,903 A | 1/1981 | Larkin |
| 4,274,415 A | 6/1981 | Kanamoto et al. |
| 4,299,224 A | 11/1981 | Noiles |
| 4,317,451 A | 3/1982 | Cerwin et al. |
| 4,340,061 A | 7/1982 | Kees, Jr. et al. |
| 4,367,746 A | 1/1983 | Derechinsky |
| 4,372,316 A | 2/1983 | Blake, III et al. |
| 4,374,523 A | 2/1983 | Yoon |
| 4,396,139 A | 8/1983 | Hall et al. |
| 4,412,539 A | 11/1983 | Jarvik |
| 4,418,694 A | 12/1983 | Beroff et al. |
| 4,425,915 A | 1/1984 | Ivanov |
| 4,427,008 A | 1/1984 | Transue |
| 4,430,997 A | 2/1984 | DiGiovanni et al. |
| 4,433,689 A | 2/1984 | Von Zeppelin |
| 4,444,187 A * | 4/1984 | Perlin ........................ 606/158 |
| 4,448,193 A | 5/1984 | Ivanov |
| 4,450,839 A | 5/1984 | Transue |
| 4,471,766 A | 9/1984 | Terayama |
| 4,471,780 A | 9/1984 | Menges et al. |
| 4,476,865 A | 10/1984 | Failla et al. |
| 4,478,218 A | 10/1984 | Mericle |
| 4,478,220 A | 10/1984 | Di Giovanni et al. |
| 4,480,641 A | 11/1984 | Failla et al. |
| 4,485,816 A | 12/1984 | Krumme |
| 4,487,205 A | 12/1984 | Di Giovanni et al. |
| 4,492,232 A | 1/1985 | Green |
| 4,493,319 A | 1/1985 | Polk et al. |
| 4,500,024 A | 2/1985 | DiGiovanni et al. |
| 4,509,518 A | 4/1985 | McGarry et al. |
| 4,512,345 A | 4/1985 | Green |
| 4,527,562 A | 7/1985 | Mericle |
| 4,550,715 A | 11/1985 | Santangelo et al. |
| 4,556,058 A | 12/1985 | Green |
| 4,556,060 A | 12/1985 | Perlin |
| 4,557,263 A | 12/1985 | Green |
| 4,562,839 A | 1/1986 | Blake, III et al. |
| 4,570,633 A | 2/1986 | Golden |
| 4,590,937 A | 5/1986 | Deniega |
| 4,616,650 A | 10/1986 | Green et al. |
| 4,616,651 A | 10/1986 | Golden |
| 4,620,541 A | 11/1986 | Gertzman et al. |
| 4,624,254 A | 11/1986 | McGarry et al. |
| 4,637,395 A | 1/1987 | Caspar et al. |
| 4,638,804 A | 1/1987 | Jewusiak |
| 4,646,741 A | 3/1987 | Smith |
| 4,658,822 A | 4/1987 | Kees, Jr. |
| 4,660,558 A | 4/1987 | Kees, Jr. |
| 4,662,373 A | 5/1987 | Montgomery et al. |
| 4,665,906 A | 5/1987 | Jervis |
| 4,671,278 A | 6/1987 | Chin |
| 4,674,504 A | 6/1987 | Klieman et al. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,741,337 A | 5/1988 | Smith et al. |
| 4,765,335 A | 8/1988 | Schmidt et al. |
| 4,777,949 A | 10/1988 | Perlin |
| 4,777,950 A | 10/1988 | Kees, Jr. |
| 4,788,966 A | 12/1988 | Yoon |
| 4,791,707 A | 12/1988 | Tucker |
| 4,796,625 A | 1/1989 | Kees, Jr. |
| 4,796,627 A | 1/1989 | Tucker |
| 4,821,721 A | 4/1989 | Chin et al. |
| 4,822,348 A | 4/1989 | Casey |
| 4,834,096 A | 5/1989 | Oh et al. |
| 4,844,066 A | 7/1989 | Stein |
| 4,854,317 A | 8/1989 | Braun |
| 4,858,608 A | 8/1989 | McGuilkin |
| 4,869,268 A | 9/1989 | Yoon |
| 4,919,152 A | 4/1990 | Ger |
| 4,934,364 A | 6/1990 | Green |
| 4,943,298 A | 7/1990 | Fujita et al. |
| 4,944,443 A | 7/1990 | Oddsen et al. |
| 4,950,258 A | 8/1990 | Kawai et al. |
| 4,961,743 A | 10/1990 | Kees, Jr. et al. |
| 4,966,603 A | 10/1990 | Focelle et al. |
| 4,967,949 A | 11/1990 | Sandhaus |
| 4,976,722 A | 12/1990 | Failla |
| 4,979,950 A | 12/1990 | Transue et al. |
| 4,983,176 A | 1/1991 | Cushman et al. |
| 5,002,563 A | 3/1991 | Pyka et al. |
| 5,026,379 A | 6/1991 | Yoon |
| 5,030,226 A | 7/1991 | Green et al. |
| 5,035,692 A | 7/1991 | Lyon et al. |
| 5,037,433 A | 8/1991 | Wilk et al. |
| 5,044,540 A | 9/1991 | Dulebohn |
| 5,053,045 A | 10/1991 | Schmidt et al. |
| 5,084,057 A | 1/1992 | Green et al. |
| 5,100,420 A | 3/1992 | Green et al. |
| 5,156,608 A | 10/1992 | Troidl et al. |
| 5,156,609 A | 10/1992 | Nakao et al. |
| 5,171,249 A | 12/1992 | Stefanchik et al. |
| 5,192,288 A | 3/1993 | Thompson et al. |
| 5,197,970 A | 3/1993 | Green et al. |
| 5,207,692 A | 5/1993 | Kraus et al. |
| 5,217,473 A | 6/1993 | Yoon |
| 5,290,299 A | 3/1994 | Fain et al. |
| 5,300,081 A | 4/1994 | Young et al. |
| 5,340,360 A | 8/1994 | Stefanchik |
| 5,342,373 A | 8/1994 | Stefanchik et al. |
| 5,364,002 A | 11/1994 | Green et al. |
| 5,366,134 A | 11/1994 | Green et al. |

| | | | | | | |
|---|---|---|---|---|---|---|
| 5,368,600 A | 11/1994 | Failla et al. | | 5,849,019 A | 12/1998 | Yoon |
| 5,389,098 A | 2/1995 | Tsuruta et al. | | 5,858,018 A | 1/1999 | Shipp et al. |
| 5,395,381 A | 3/1995 | Green et al. | | 5,897,565 A | 4/1999 | Foster |
| 5,431,668 A | 7/1995 | Burbank, III et al. | | 5,921,997 A | 7/1999 | Fogelberg et al. |
| 5,431,669 A | 7/1995 | Thompson et al. | | 5,993,465 A | 11/1999 | Shipp et al. |
| 5,439,468 A | 8/1995 | Schulze et al. | | 6,159,223 A | 12/2000 | Danks et al. |
| 5,474,567 A | 12/1995 | Stefanchik et al. | | | | |
| 5,514,149 A | 5/1996 | Green et al. | | | | |
| 5,527,318 A | 6/1996 | McGarry | | | | |
| 5,527,319 A | 6/1996 | Green et al. | | | | |
| 5,542,949 A | 8/1996 | Yoon | | | | |
| 5,547,474 A | 8/1996 | Kloeckl et al. | | | | |
| 5,593,414 A | 1/1997 | Shipp et al. | | | | |
| 5,601,573 A | 2/1997 | Fogelberg et al. | | | | |
| 5,601,574 A | 2/1997 | Stefanchik et al. | | | | |
| RE35,525 E | 6/1997 | Stefanchik et al. | | | | |
| 5,681,330 A | 10/1997 | Hughett et al. | | | | |
| 5,700,270 A | 12/1997 | Peyser et al. | | | | |
| 5,700,271 A | 12/1997 | Whitfield et al. | | | | |
| 5,702,408 A | 12/1997 | Wales et al. | | | | |
| 5,833,700 A | 11/1998 | Fogelberg et al. | | | | |
| 5,843,097 A | 12/1998 | Mayenberger et al. | | | | |

FOREIGN PATENT DOCUMENTS

| | | |
|---|---|---|
| DE | 2330182 | 1/1975 |
| DE | 3722311 | 1/1989 |
| DE | 3802651 | 8/1989 |
| EP | 0 681 810 | 11/1995 |
| GB | 2071751 | 9/1981 |
| JP | 6-237939 | 8/1994 |
| SU | 1389762 | 4/1988 |
| WO | WO 87/06118 | 10/1987 |
| WO | WO 90/02522 | 3/1990 |
| WO | WO 90/03763 | 4/1990 |
| WO | WO 95/05778 | 3/1995 |
| WO | WO 88/0148 | 3/1998 |

\* cited by examiner

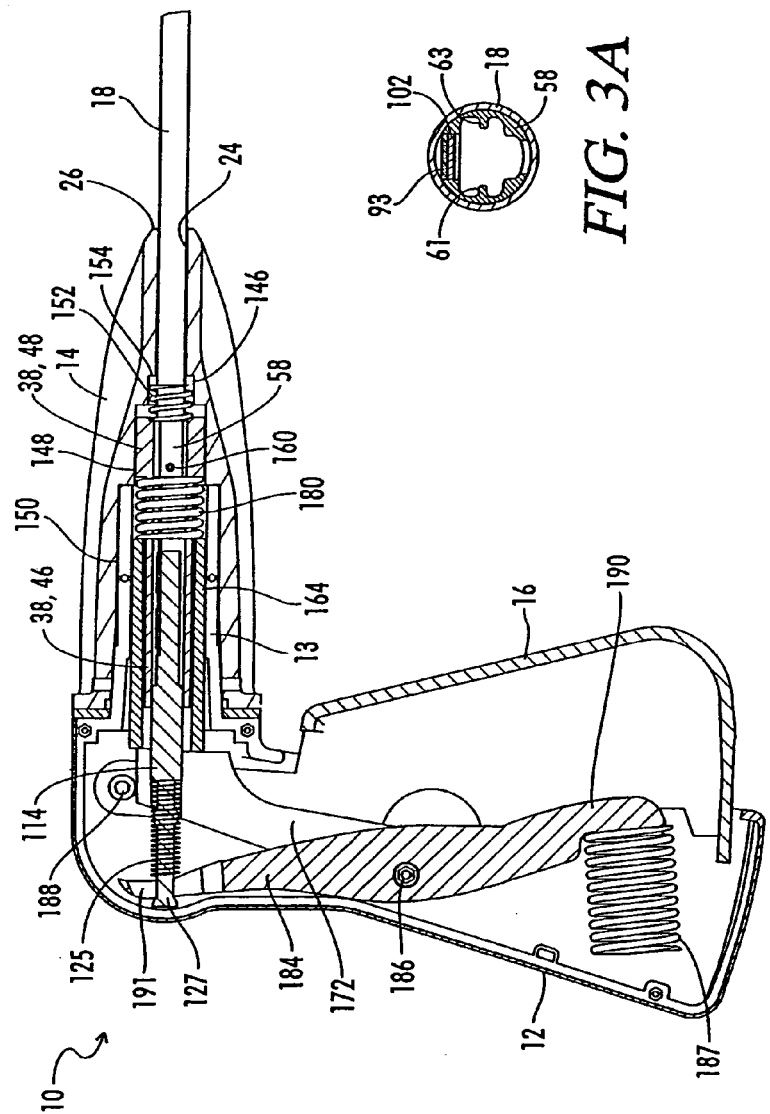
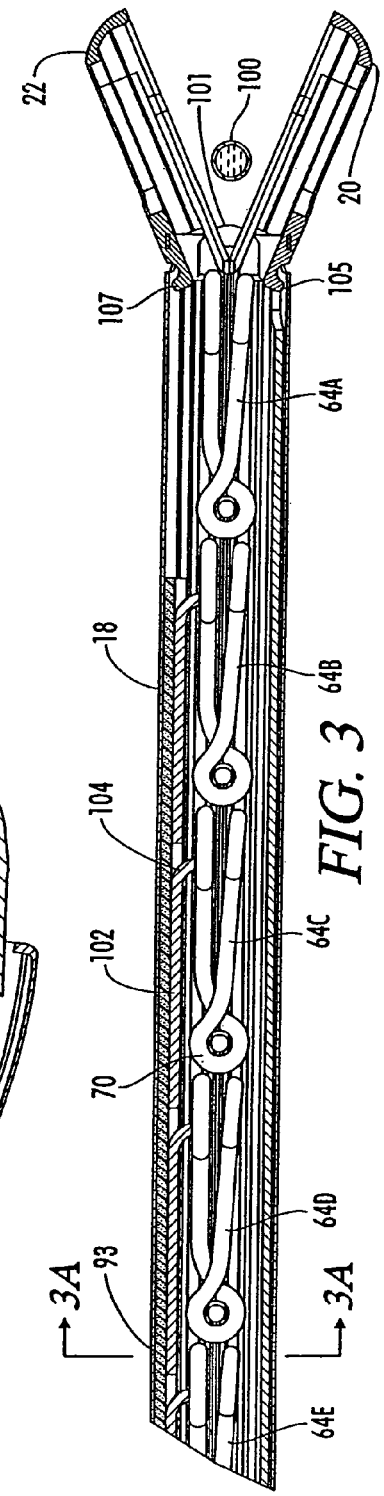

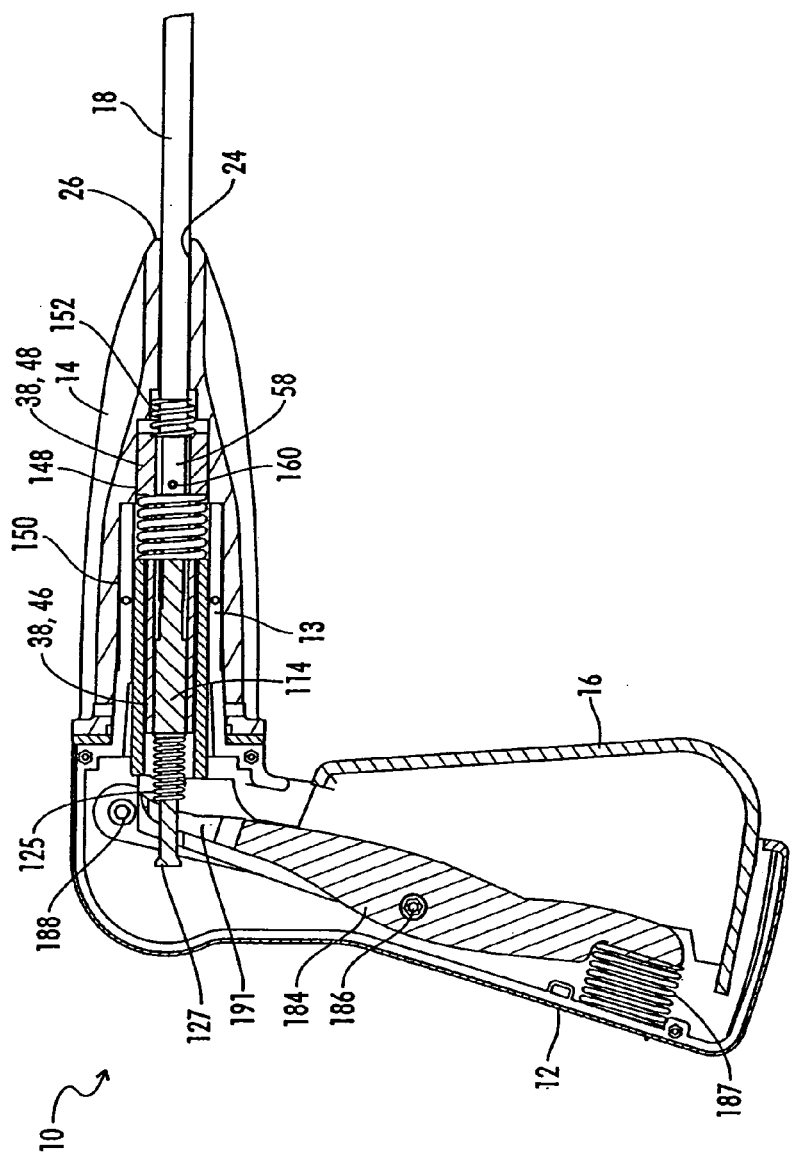
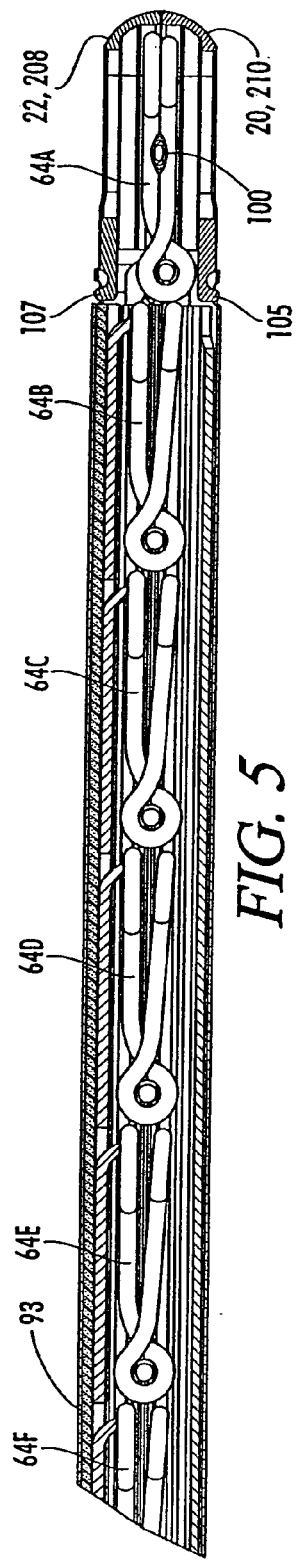
FIG. 4
FIG. 5

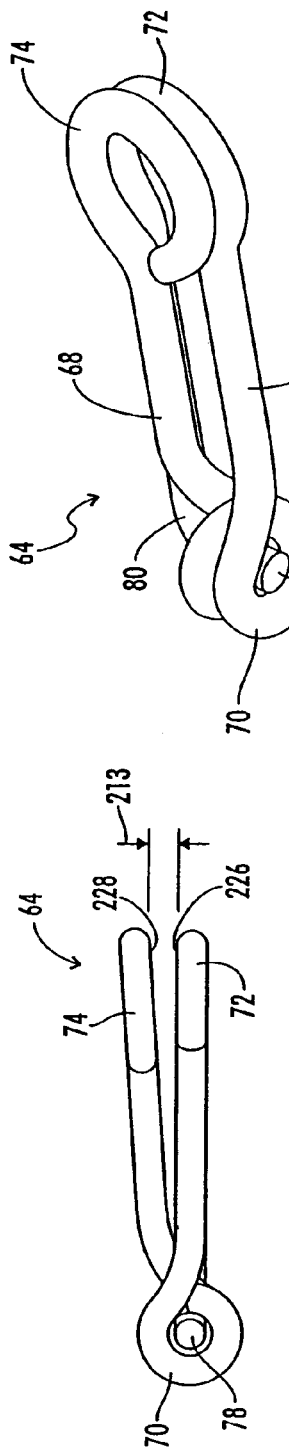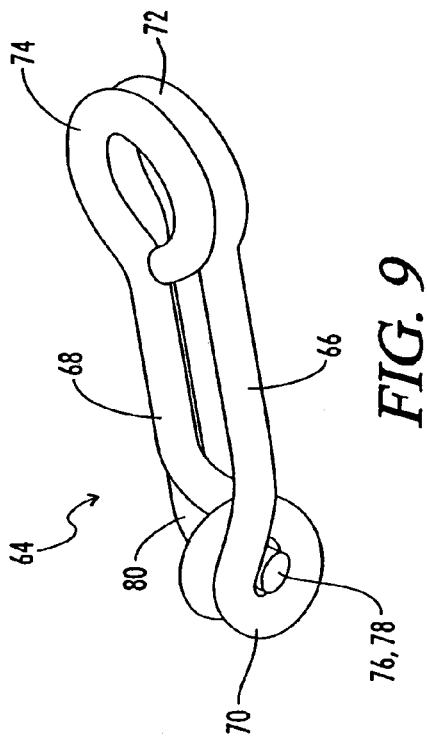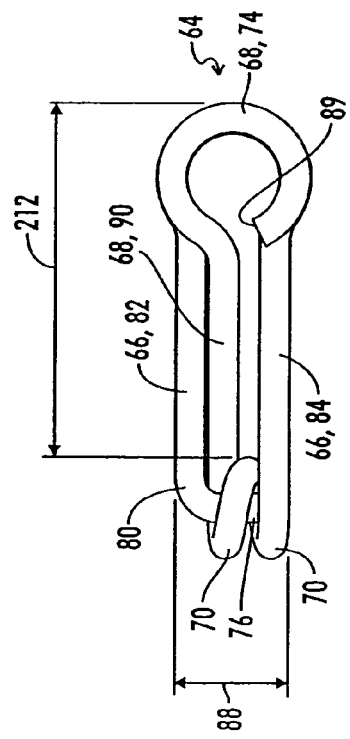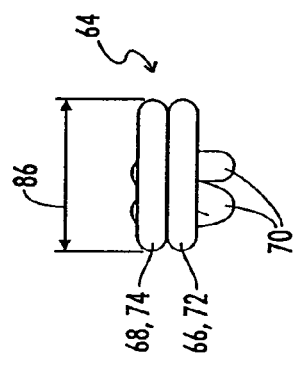

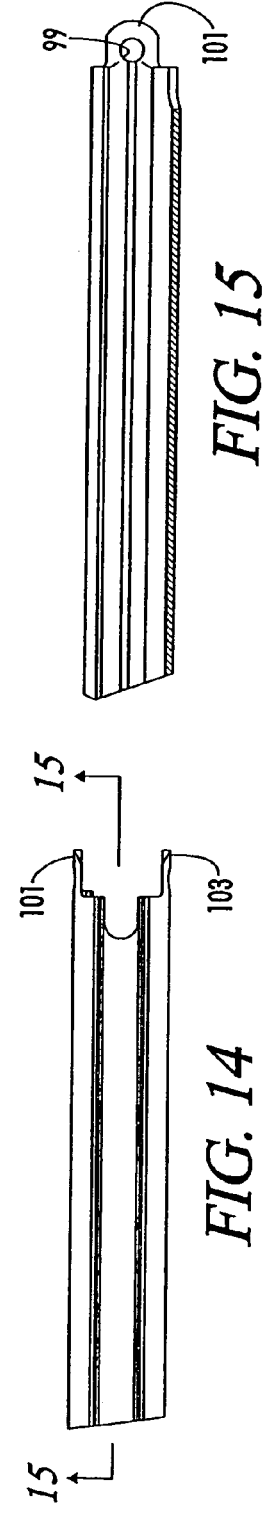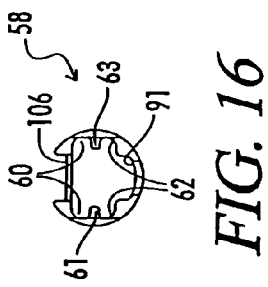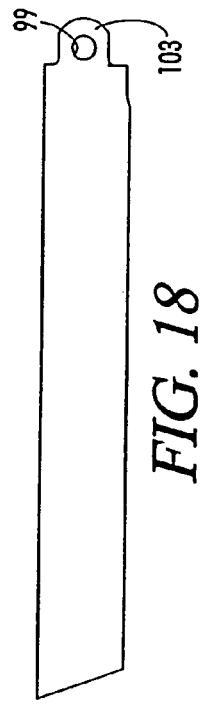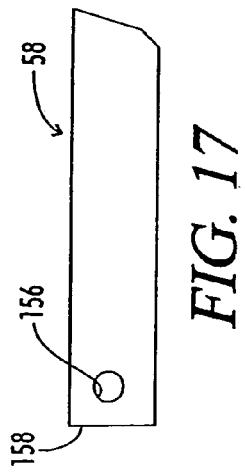
FIG. 13
FIG. 15
FIG. 18
FIG. 16
FIG. 14
FIG. 17

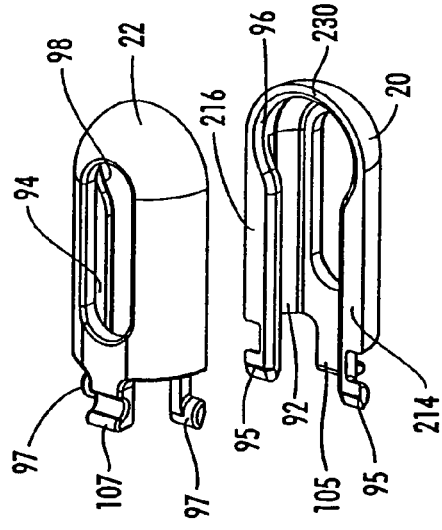
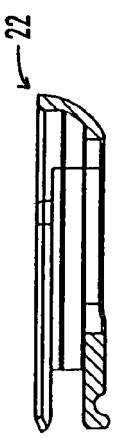
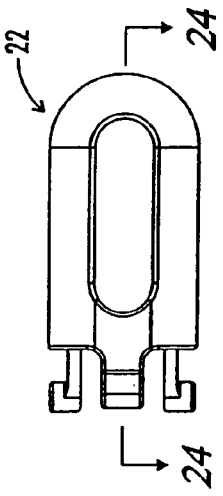
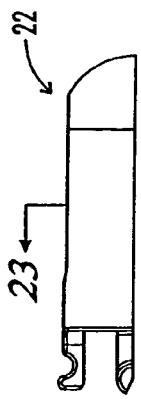
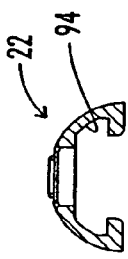
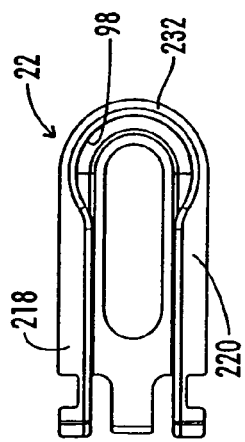

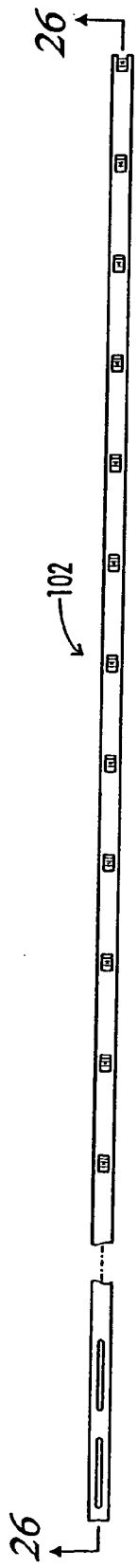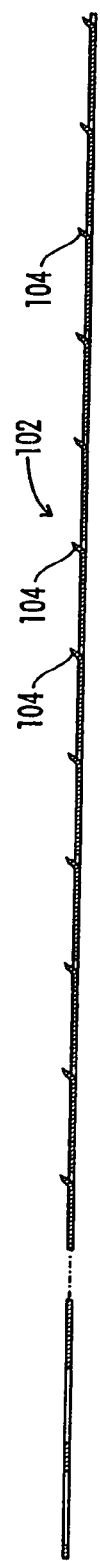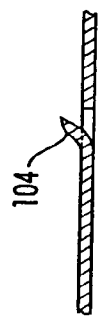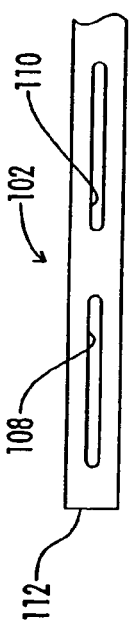
FIG. 25
FIG. 26
FIG. 27
FIG. 28

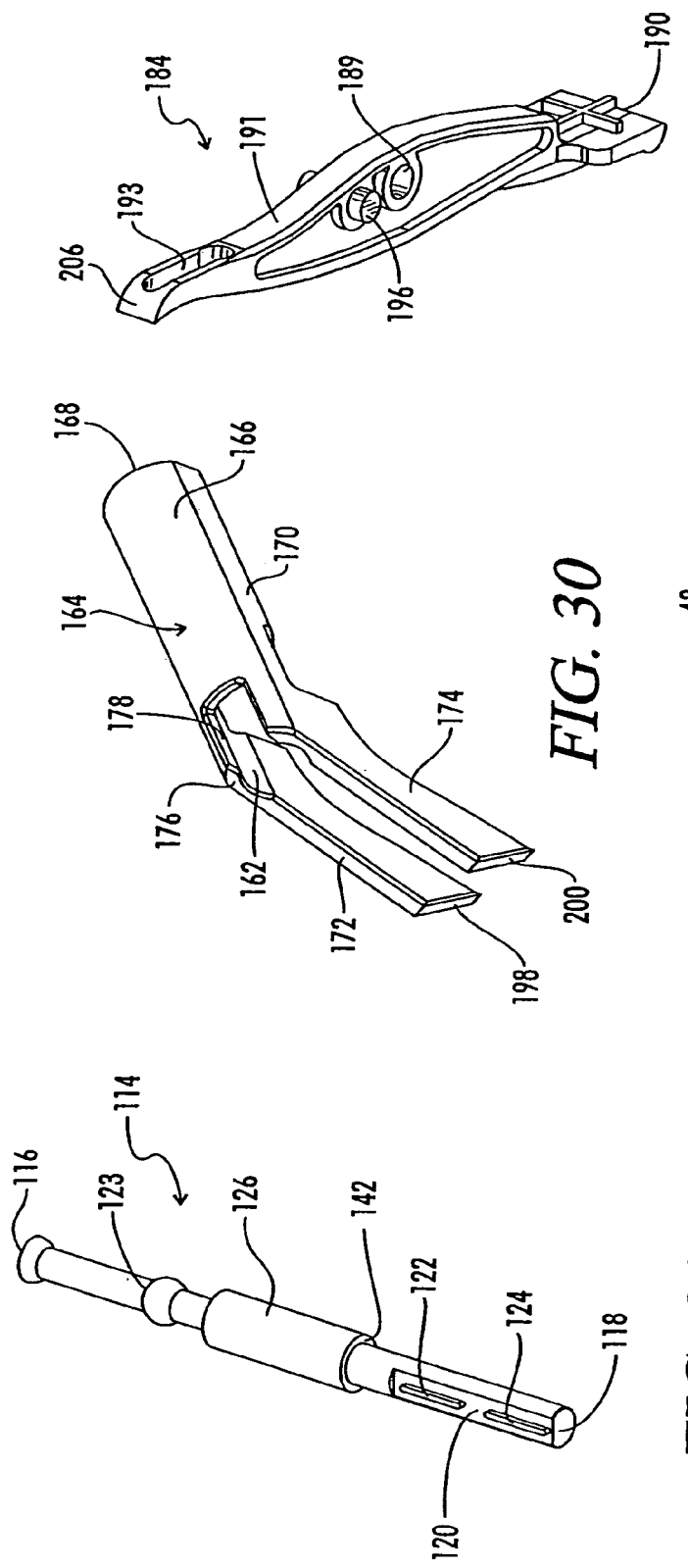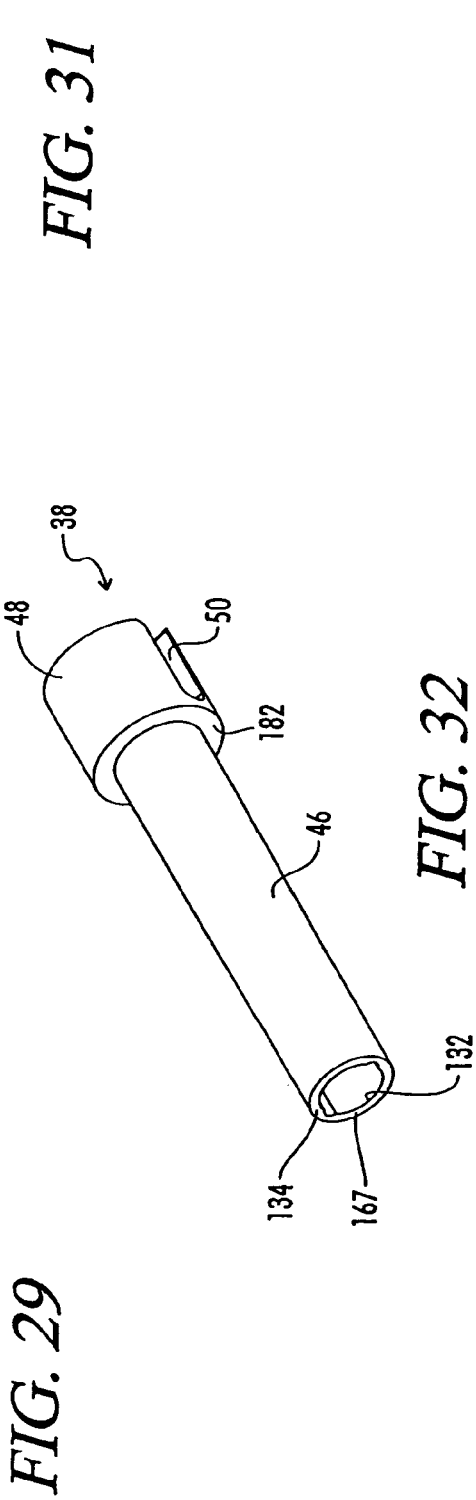

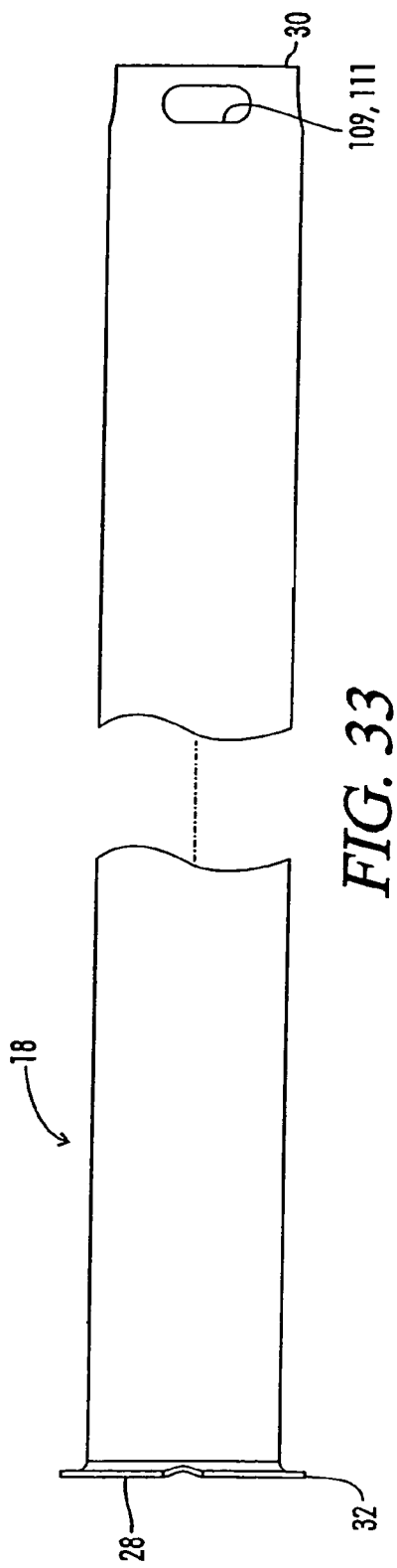
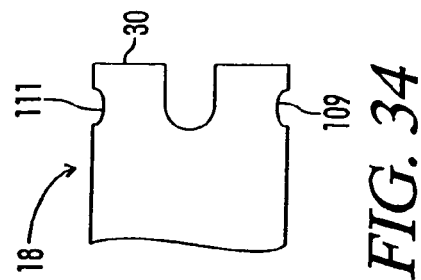
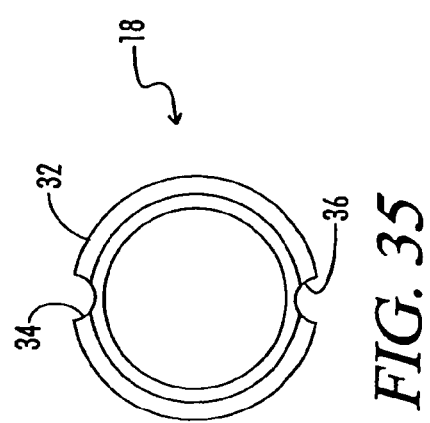
FIG. 33
FIG. 34
FIG. 35

LIGATION CLIP AND CLIP APPLIER

This application is a continuation of application Ser. No. 10/082,915, filed Feb. 25, 2002, now U.S. Pat. No. 6,652,545; which is a divisional of application Ser. No. 09/258,943, filed Mar. 1, 1999, now U.S. Pat. No. 6,350,269; all of which are incorporated herein by reference.

BACKGROUND OF THE INVENTION

1. Field of the Invention

The present invention relates generally to mechanical devices used in surgical procedures to obtain ligation or hemostasis, and more particularly, to low profile tools that can apply a pre-formed, spring loaded ligation clip used during surgery to clamp around a vessel or duct, such as the cystic duct, and thereby obtain ligation.

2. Description of the Prior Art

It will be appreciated by those skilled in the art that the use of ligation clips to control bleeding during surgical procedures is will known. As described, for example, in U.S. Pat. Nos. 4,976,722 and 4,979,950 prior art clips are generally formed of metal wire, usually a titanium alloy, having a "U-shaped" rectangular cross-section. Such prior art clips often include a grooved pattern machined into the inner or clamping surfaces of the clip, in an attempt to enhance the ability of the clip to remain in position after it is closed around the vessel. Application of the clip to the vessel is normally effected by means of a crushing action produced by a clip applier, such as the disclosed in U.S. Pat. No. 5,030,226. Such crushing actions, of course, permanently deform the clips, making them difficult to remove or re-position.

Prior art surgical ligation clips have several inherent problems. For example, the force applied by the clip to the vessel can be variable and inconsistent from one clip to the next, because of the variation in crushing force applied to the clip by the user. Further, prior art clips have a tendency to slip off the end of the blood vessel stub (i.e., perpendicular to the axis of the vessel) to which it has been applied, because of the low coefficient of friction associated with the clip, and lack of adequate restraining force provided by the clip. Because of this, separation of the clip from the vessel to which it has been applied, after the wound has been closed, is not uncommon. A related problem found in the prior art is the fact that the ligating or restraining force offered by the crushed clip varies along the length of the clip, decreasing toward the open end. Thus, the section of the vessel near the open end of the clip can be inadequately ligated.

It is also common in the prior art to actually form and crush the clip only at the time of its application to the targeted blood vessel. It is often required that the vessels of 4 mm and larger diameter be ligated. Because most clips of the prior art have no spring action it is required that the inside clearance dimension of the clip, prior to crushing, be larger than the vessel. This does not lend itself to clip applier designs that will pass through small 5 mm trocars. The applier must be inserted through a trocar placed through the patient's external tissues and into the surgical field. Thus, prior art ligation clip appliers used in laparoscopic procedures universally consist of a 10 mm diameter clip applier that can fit only through a trocar having a 10 to 11 mm diameter entry port. Because one goal of laparoscopic surgery is to minimize the size of the entry wound, a surgical ligation clip and clip applier that can be used within a 5 mm or even a 2.5 mm diameter trocar port is highly desirable.

New minimally invasive surgical procedures and the need for less invasiveness for current procedures require the development of smaller and smaller devices. The harvesting of saphalous veins and certain cardiovascular procedures would benefit from reduced diameters trocars, below 3 mm diameter.

To address these problems a new spring action surgical clip was designed, as illustrated in FIGS. 1 and 2 in U.S. Pat. No. 5,593,414, which is assigned to the assignee of the present invention and is incorporated herein by reference. This clip has a vessel clamping arm, a vessel support member, and at least one tension coil integrally joining the arm and support member. The clip is pre-formed so that in its equilibrium state, it can be easily placed within the surgical field, including through an endoscopic trocar port with as little as 5 mm diameter. After the clip is placed proximate the blood vessel or duct to be clamped, the clamping arm is moved from its equilibrium position to a position under higher tension, allowing positioning of the vessel between the arm and support member. When correct placement and positioning is achieved, the arm is released and, as the arm tends to move back towards its equilibrium position, it clamps the vessel between the arm's curved lower surface and the supporting upper surface of the vessel support member.

To enhance the performance of the tension coil(s), the vessel support member includes first and second arms, one of which terminates in a 180° bend section. Minimal cross-sectional area of the clip is achieved by substantially longitudinally aligning the vessel support member, the clamping arm, the 180° bend section, and the tension coil.

The clamping arm is pre-formed into an equilibrium that generally aligns with the horizontal plane of the support member. A second embodiment of the clip pre-loads the clamping arm into a pre-loaded equilibrium position where the free end of the arm rests against the upper surface of the support member.

There exists a relationship between the diameter of the trocar (hence the applier tube) and the maximum diameter of a vessel that can be ligated. Older crush clip technology limits the ratio of wound size to maximum diameter to be ligated to greater than 2. That is, to ligate a 5 mm vessel a puncture wound of 10–12 mm is required. U.S. Pat. No. 5,593,414 teaches the method of using a spring clip that is inserted into the surgical field in the closed state, opened over a vessel, the diameter of which has been reduced, or preclamped, by the tool, and closed over the preclamped vessel. This method allows an entry wound to vessel diameter of 1 or smaller. Thus, a 5 mm vessel can be ligated through a 5 mm trocar, substantially less invasive as compared to the older crush clip technology. For a trocar diameter of 2.5 mm the clip can be scaled down to approximately half size on the wire diameter, coil height, and length and still supply an acceptable ligation force on a 2.5 mm vessel.

Unfortunately, several problems are encountered in applying the spring-action ligation clip of U.S. Pat. No. 5,593,414 to a vessel through a 5 mm or small trocar port. First, the nominal 5 mm cross-section of the clip that is inserted through the trocar places severe design restrictions on any applier mechanism. Second, care must be taken so that the elastic limit of the spring material is not exceeded when the clip is opened up so that it can be placed over the vessel diameter. For the titanium wire of diameter 0.75 mm, for example, lifting the distal end of the center leg of the spring much above a few mm will exceed the elastic limit. Secondly, these spring clips are small and compact and owing to the pre-load, have a great deal of energy stored in the spring. As these clips are opened to place them over a vessel the stored energy increases substantially, in some cases more than doubling. This energy makes controlling the clip, to insure proper installation, difficult. Undesirable translation or rotation can result in misplacement or dropping of the clip inside the body.

What is needed, then, is a spring clip that includes a means that allows positive control of the clip during the installation process and a clip applier tool that can be used to place a pre-formed spring action ligation clip around a large diameter vessel without permanently deforming or weakening the clip, one that will compress, without crushing the vessel, and yet be small enough to use in through a 5 mm or smaller trocar. Also needed is a design which will avoid the mechanical difficulty of opening the clips prior to placement of the clips on the vessel.

Another approach which has been proposed to provide smaller diameter endoscopic clip application is that of U.S. Pat. No. 5,601,573 to Fogelberg et al. Fogelberg et al. still struggles with the complex manipulation required to advance the clip in a closed position and then open the clip prior to placement. Fogelberg et al. also has an overly-complex multi-stage trigger arrangement for actuation of the jaws and the clip advancement mechanism. The present invention presents several improvements over Fogelberg et al. including: (1) advancement of the clips in their open position rather than a closed position; and (2) a smooth single stage trigger action which simultaneously closes the jaws and advances the fowardmost clip into the jaws. Another difference between the present invention and Fogelberg et al., is that Fogelberg pushes a stack of clips, whereas the present invention individually engages and pushes each clip simultaneously, thus yielding better control of the clips.

SUMMARY OF THE INVENTION

A surgical ligation clip constructed in accordance with the present invention includes support member and the clamping arm with a connector, such as a coil spring, joining the support member and the clamping arm. The clip includes first and second enlarged ends defined on the support member and the clamping arm respectively. The enlarged ends are first and second wire loops integrally formed with the support member and the clamping arm of the clip. These enlarged ends provide first and second control surfaces.

Clips such as the one just described are received in an open position in a magazine of a clip applier. The magazine has first and second longitudinally extending, partially closed channels. The enlarged ends of the spring clip are received in and trapped within the first and second channels of the magazine which hold the clip in its open position.

First and second articulated jaws are attached to the magazine. The jaws have channel extensions therein aligned with the first and second channels of the magazine, so that the clip can be received from the magazine in the jaws with the first and second control surfaces or enlarged ends of the support member and the clamping arm being received in the first and second channel extensions of the jaws.

The first and second channel extensions of the jaws include first and second releasing openings, respectively, which are larger than the first and second enlarged ends of the support member and the clamping arm, so that when the clip is pushed forward in the jaws to a position where the control surfaces are aligned with the releasing openings, the support member and the clamping arm are released thereby allowing the spring to move the support member and the clamping arm toward each other to ligate a blood vessel or other body duct therebetween.

An actuator is operably associated with the jaws and movable between a first position in which the jaws are open, and a second position in which the jaws are closed.

It is therefore an object of the present invention to provide an improved surgical ligation clip and applicator assembly.

Another object of the present invention is the provision of improved surgical ligation clips.

Still another object of the present invention is the provision of improved surgical ligation clip applicator tools.

And another object of the present invention is the provision of improved methods of ligating blood vessels and ducts.

Still another object of the present invention is the provision of improved ligation clips and applicator tools which are capable of being inserted through relatively small openings in the body, 5 mm diameter or smaller.

Another object of the present invention is the provision of apparatus and methods whereby the spring clip is held in its open position as it is advanced through the magazine of the apparatus.

Yet another object of the present invention is the provision of an improved clamping jaw design having first and second spaced clamping points along the length of the lumen.

Still another object of the present invention is the provision of improved methods of ligating a lumen including preclamping the lumen at first and second spaced clamping points, then placing a spring clip over the lumen and clamping the lumen with a spring clip at a third point located between the first and second points.

Still another object of the present invention is the provision of apparatus and methods for ligating a stub end of a lumen.

Other and further objects, features and advantages of the present invention will be readily apparent to those skilled in the art upon a reading of the following disclosure when taken in conjunction with the accompanying drawings.

BRIEF DESCRIPTION OF THE DRAWINGS

FIG. 2 is an enlarged sectioned view of the upper portion of the applicator barrel, with the trigger in the 0% engaged position.

FIG. 3 is an enlarged sectioned view of the operating end of the applicator corresponding to the 0% engaged position of the trigger in FIG. 2, and showing the jaws in their open position.

FIG. 3A is a cross-sectional view taken along line 3A—3A of FIG. 3.

FIG. 4 is a is an enlarged section view of the upper portion of the applicator with the trigger in the 100% engaged position.

FIG. 5 is an enlarged sectioned view of the operating end of the applicator corresponding to the 100% engaged position of the trigger in FIG. 3, and showing the jaws in their closed position.

FIG. 8 is a side elevation view of the ligation clip used with the apparatus of FIG. 1, showing the ligation clip with the support member and the clamping arm in an open position.

FIG. 9 is a perspective view of the clip of FIG. 8 with the support member and the clamping arm in a fully closed or pre-loaded equilibrium position.

FIG. 10 is a top plan view of the clip of FIG. 8.

FIG. 11 is a side elevation view of the clip of FIG. 10 in a closed position.

FIG. 12 is a right end elevation view of the clip of FIG. 10 in a closed position.

FIG. 13 is a perspective view of the clip magazine of the apparatus of FIG. 1.

FIG. 14 is an enlarged top plan view of the right end portion of the magazine of FIG. 13.

FIG. 15 is an elevation sectioned view taken along line 15—15 of FIG. 14.

FIG. 16 is a right end view of the magazine of FIG. 14.

FIG. 17 is an enlarged side elevation view of the left end portion of the magazine of FIG. 13.

FIG. 18 is an enlarged side elevation view of the right end portion of the magazine of FIG. 13.

FIG. 19 is a perspective view of a pair of jaws of the apparatus of FIG. 1.

FIG. 20 is a top plan view of the top jaw of FIG. 19.

FIG. 21 is a front elevation view of the jaw of FIG. 20.

FIG. 22 is a bottom view of the jaw of FIG. 20.

FIG. 23 is a sectioned elevation view of the jaw taken along line 23—23 of FIG. 21.

FIG. 24 is an elevation longitudinally sectioned view of the top jaw taken along line 24—24 of FIG. 20.

FIG. 25 is a plan view of the elongated pusher rod.

FIG. 26 is an elevation sectioned view of the pusher rod taken along line 26—26 of FIG. 25 and showing the upturned prongs.

FIG. 27 is an enlarged view of one of the upturned prong portions.

FIG. 28 is an enlarged view of the left end portion of the pusher rod of FIG. 25.

FIG. 29 is a perspective view of the pusher rod piston.

FIG. 30 is a perspective view of the primary outer tube piston.

FIG. 31 is a perspective view of the actuator.

FIG. 32 is a perspective view of the intermediate outer tube piston.

FIG. 33 is a top plan view of the outer tube.

FIG. 34 is a front elevation view of the right end portion of the outer tube of FIG. 33.

FIG. 35 is a left end view of the outer tube of FIG. 33.

DETAILED DESCRIPTION OF THE PREFERRED EMBODIMENTS

Figure 1:
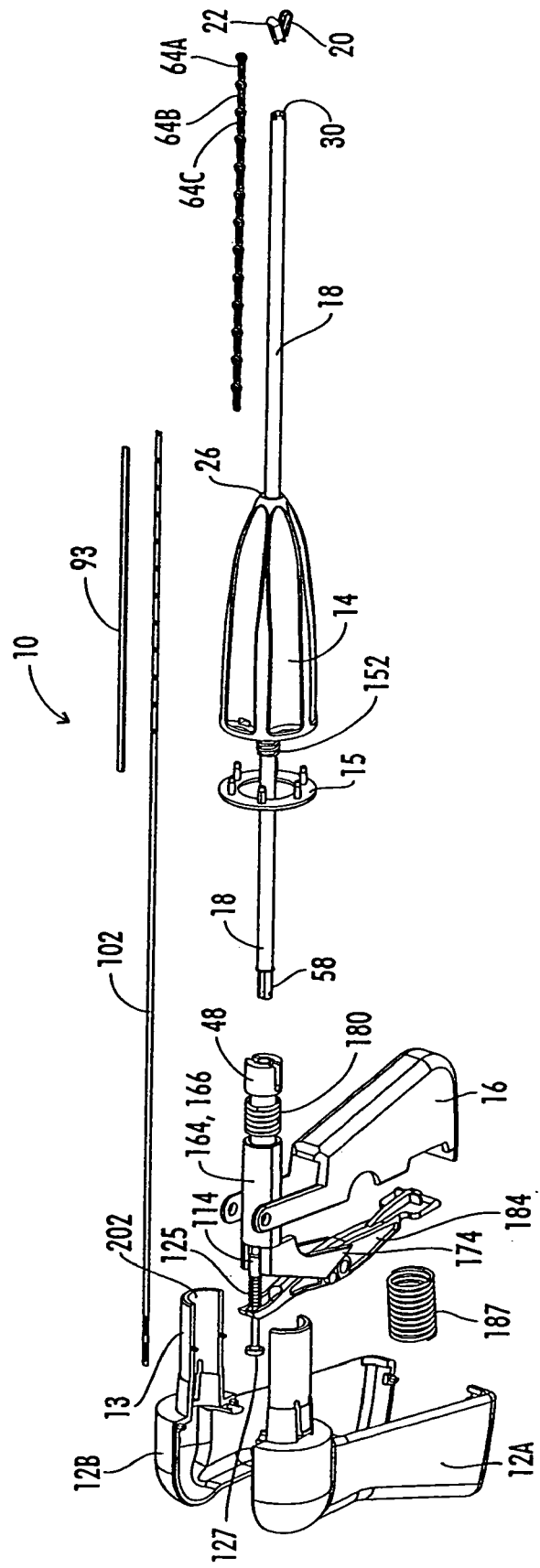
FIG. 1 is an exploded view of the clip applicator of the present invention.
Figure 6:
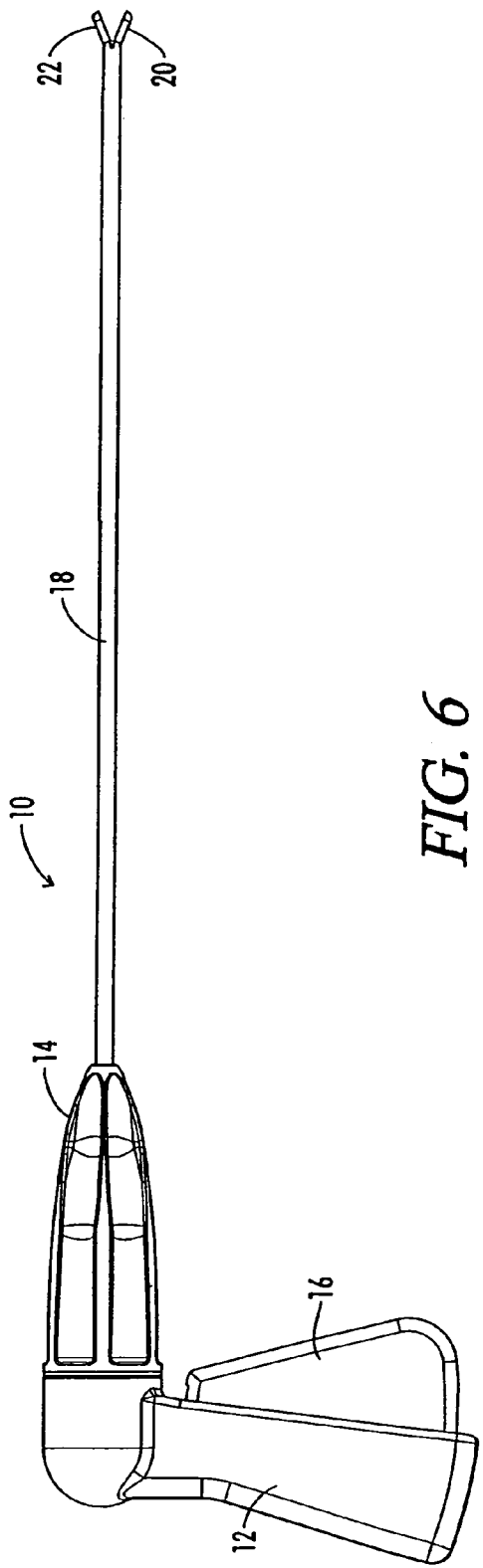
FIG. 6 is an elevation view of the apparatus of FIG. 1, with the jaws in the open position.
Figure 7:
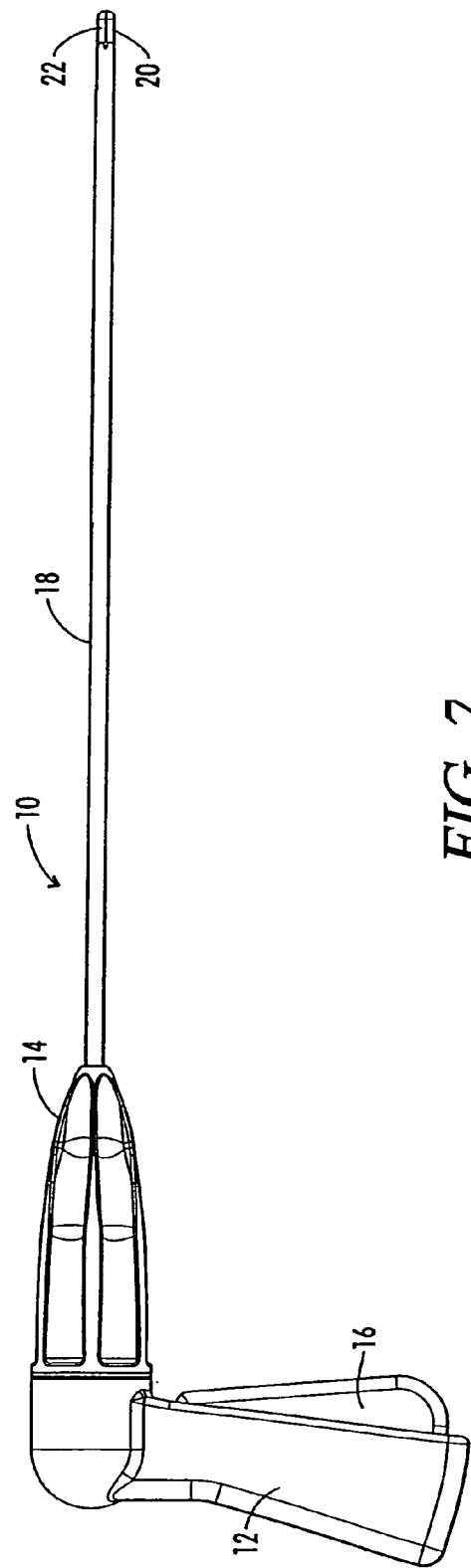
FIG. 7 is an elevation view of the apparatus of FIG. 1, with the jaws in the closed position.

Referring now to the drawings, and particularly to FIGS. 1–7, a surgical clip applicator apparatus is there shown and generally designated by the numeral 10. The apparatus 10 includes a body or handle portion 12, a barrel portion 14, a trigger 16, an outer tube 18, and first and second articulated jaws 20 and 22.

As seen in the exploded view of FIG. 1, the handle portion 12 is formed from two molded plastic handle portion halves 12A and 12B. A cylindrical forwardly extending handle projection 13 is integrally formed with the handle 12. A barrel 14 which is also referred to as a rotator 14, is received over the cylindrical extension 13. A rotator ring 15 is attached to the rear end of the barrel 14. The barrel or rotator 14 and the attached tube 18, can be rotated about its longitudinal axis relative to handle 12.

It is noted that in this disclosure the terms forward and rearward are utilized from the viewpoint of a person holding the apparatus 10, so that the forward end 26 of the barrel 14 faces away from the person who is holding the handle 12 and trigger 16 is in their hand while pointing the apparatus 10 away from themselves.

The inner details of construction of the apparatus 10 are best seen in the enlarged sectioned views of FIGS. 2–5.

The barrel 14 has a bore 24 defined through its forward end 26. The outer tube 18 is received in the barrel bore 24, and is slidable therein as is further described below.

The details of construction of the outer tube 18 are best shown in FIGS. 33–35. Outer tube 18 has a rearward end 28 and a forward end 30. The rearward end 28 includes an annular flange 32.

As seen in FIG. 35, the flange 32 has a couple of orientation recesses 34 and 36 defined therein.

Figure 39:
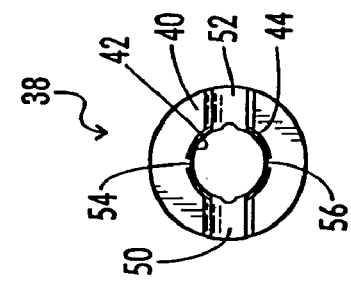
FIG. 39 is a forward end view of the intermediate outer tube piston of FIG. 32.

The flanged rear end 28 of outer tube 18 is attached to an intermediate outer tube piston 38. The piston 38 may also be referred to as a jaw pusher 38. The details of construction of piston 38 are best seen in FIGS. 32 and 39. FIG. 39 is a forward end view of piston 38, and as shown there, the forward end 40 of piston 38 has a bore 42 and a counterbore 44 defined therein. As seen in FIG. 32, the piston 38 has a smaller diameter rearward portion 46 and a larger diameter forward portion 48. The larger diameter forward portion 48 has a pair of diametrically opposed slots 50 and 52 defined therein, the purpose of which is further described below.

The attachment of the outer tube 18 to the intermediate outer tube piston 38 is accomplished by closely receiving the flange 32 of the rearward end of tube 18 within the counter bore 44 of piston 38 so that the orientation recesses 34 and 36 fit over orientation bumps 54 and 56 (see FIG. 39) defined on the piston 38. Thus, as the intermediate outer tube piston 38 is pushed forward it pushes against the flange 32 of tube 18 thus moving the tube 18 forward and compressing return spring 152. As the tube 18 moves forward it pivots the jaws closed. On release of the trigger 16, the return spring 152 pushes the tube 18 rearward so that it follows the rearward movement of piston 38.

Concentrically contained within the outer tube 18 is a clip magazine 58. The details of construction of the magazine 58 are shown in FIGS. 13–18. As best shown in the end view of FIG. 16, the magazine 58 is a one piece tubular member which has first and second longitudinally extending partially closed channels 60 and 62 defined therein.

The channels 60 and 62 are partially closed by radially inward extending longitudinal ledges 61 and 63. Thus each channel such as channel 60 has an inner dimension which is greater than the width of the opening between ledges 61 and 63 thus allowing an enlarged end such as the loops 72 and 74 of clip 64 to be trapped within the channels 60 and 62.

The details of construction of the clips 64 are best seen in FIGS. 8–12.

The clip 64 is shown in FIG. 8 in an open position and in FIG. 9 in a closed or pre-loaded equilibrium position. FIGS. 10, 11 and 12 are top, front and end views of the clip of FIG. 9 in the closed position.

The clip 64 includes a support member 66 and a clamping arm 68. A coil tension spring 70, which may also be generally referred to as a connector 70, joins the support member 66 and clamping arm 68.

Support member 66 has a first enlarged end 72 defined thereon. Clamping arm 68 has a second enlarged end 74 defined thereon. The first and second enlarged ends 72 and 74 are first and second wire loops which are integrally formed with the support member 66 and clamping arm 68 of clip 64.

The loops 72 and 74, and particularly the laterally outer portions thereof, may be described as first and second control surfaces 72 and 74 defined on the support member 66 and clamping arm 68, respectively, the first and second control surfaces 72 and 74 being received in and trapped within the first and second channels 60 and 62, respectively. As best seen in FIG. 5, a plurality of ligating clips 64 are received in the magazine 58, in their open position. For ease of identification, consecutive clips beginning with the fowardmost one are designated as 64A, 64B, 64C, etc. The control surfaces 72 and 74, as engaged by channels 60 and 62, prevent rotation and yawing of the clip 64 as the clip is moved through the magazine 58.

The connector 70 is preferably a coil spring biasing means which has a preload which biases the support member 66 and clamping arm 68 toward each other. The preload is preferably such that when the clip 64 is in the fully closed or pre-loaded equilibrium position shown in FIG. 9, there is still a spring preload in connector 70 which forces the wire loops 72 and 74 against each other.

The spring 70 preferably provides a preload force between the support member 66 and clamping arm 68 of at least 100 grams force when the support member 66 and clamping arm 68 are in a closed or pre-loaded equilibrium position as shown in FIG. 9.

The clip 64 is preferably formed from a single length of wire. The clip 64 includes a transverse spindle 76 having a first free end 78 and terminating in a bend 80 which leads to a first longitudinal member 82 which terminates in first wire loop 72 which leads to a second longitudinal member 84 lying parallel to first longitudinal member 82 and spaced therefrom. The first wire loop 72 has a transverse dimension or width 86 (see FIG. 12) greater than a transverse distance 88 (see FIG. 10) across the first and second longitudinal members 82 and 84. The second longitudinal member 84 terminates in the coil spring connector 70 which is wrapped around the transverse spindle 76. The coil spring connector 70 leads to a third longitudinal member 90 which terminates in the second wire loop 74 which terminates in a second free end 89.

The support member 66 can be described as including two parallel spaced apart lengths of wire 82 and 84 lying in a first plane, and the clamping arm 68 can be described as including a single length of wire 90 which pivots about the spring 70 in a second plane normal to the first plane and intersects the first plane between the two parallel spaced apart lengths of wire 82 and 84 of the support member 66. The clip 64 preferably has a throat length 212 (see FIG. 10) of no greater than about 10 mm.

Figure 36:
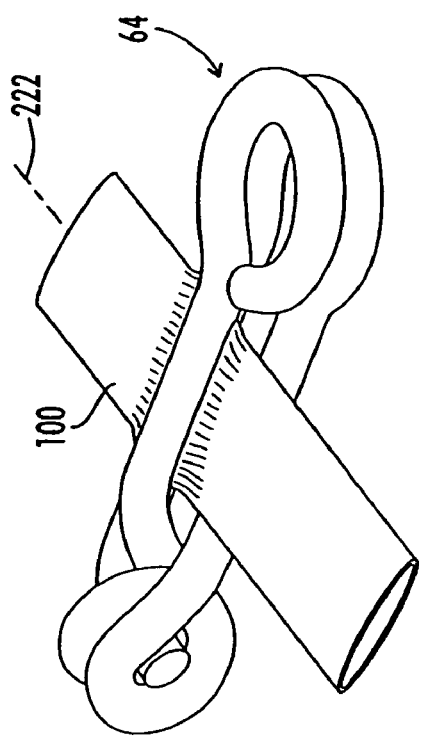
FIG. 36 is a top plan view of the clip of FIGS. 8–12 in place about a lumen which has been ligated between the support member and the clamping arm.

It is noted that the construction of clip 64 actually provides a double ligation of the vessel 100 as seen in FIG. 36. One ligation is formed between longitudinal members 82 and 90, and a second ligation is formed between longitudinal members 84 and 90.

The manner in which the clips 64 are received in magazine 58 is best seen in FIGS. 3 and 5. There it is apparent that the first and second wire loops 72 and 74 are received in the first and second channels 60 and 62, respectively, of magazine 58 with the clip 64 in an open position. The opening distance 213 is best seen in FIG. 8. Distance 213 is approximately 0.75 mm.

It is noted that the clip 64 only needs to be open the relatively small distance 213 because the vessel or lumen 100 (see FIGS. 36–38) being clamped will already be pre-clamped by jaws 20 and 22.

Also, it can be seen in FIG. 3 that the coil spring 70, the coils of which stand generally vertically in the plane of FIG. 3 are partially received in a recess 91 of the magazine 58. The recess 91 is best shown in FIG. 16.

The manner in which the wire loops 72 and 74 are received in channels 60 and 62 prevents rotation of the clips 64 as they move longitudinally through the length of magazine 58. The biasing force of spring 70 causes the loops 72 and 74 to grip the ledges 61 and 63 which provides a frictional resistance to movement of the clips through the magazine 58.

The manner in which the clips 64 are moved along the length of the magazine 58 is further described below, but first the complementary relationship between the magazine 58 and the first and second jaws 20 and 22 will be described.

The jaws 20 and 22 are best shown in FIGS. 19–24. It is noted that the jaws 20 and 22 are identical, and so the details of construction of only one of them will be described.

The jaws 20 and 22 have first and second channel extensions 92 and 94 defined therein which are aligned with the first and second channels 60 and 62 of magazine 58 when the jaws are in their closed position. The shape of second channel extension 94 is best shown in the cross-sectional view of FIG. 23. The channel extensions permit the clips 64 to be pushed forward out of the channels 60 and 62 of magazine 58 into the jaws 20 and 22 with the first and second wire loops 72 and 74 being received in the first and second channel extensions 92 and 94 of the jaws.

Figure 37:
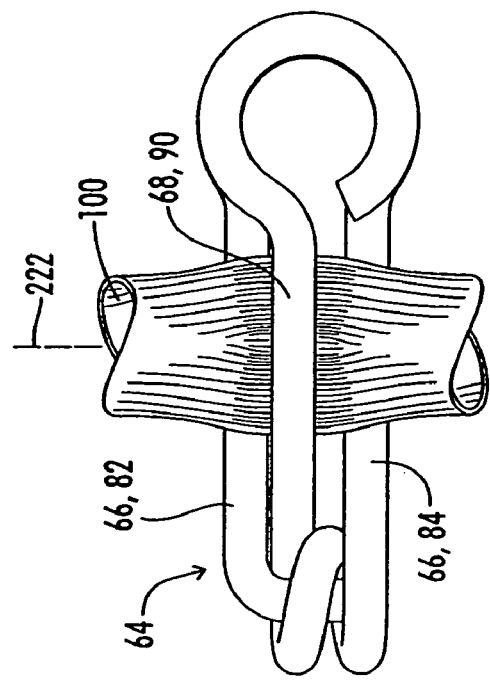
FIG. 37 is a perspective view of the clip and lumen of FIG. 36.

The first and second channel extensions 92 and 94 further include first and second releasing openings 96 and 98. It is noted that the releasing openings 96 and 98 are generally circular in shape and are of a larger diameter than are the wire loops 72 and 74. Thus, when the clip 64 is pushed forward into the jaws 20 and 22 until the wire loops 72 and 74 are aligned with the releasing openings 96 and 98, the support member 66 and clamping arm 68 will be released thus allowing the support member 66 and clamping arm 68 to move toward each other due to the force from coil spring 70, thus closing the clip 64. As the support member 66 and clamping arm 68 move toward each other they may ligate a lumen 100 therebetween as seen in FIGS. 36 and 37.

First jaw 20 has a pair of pivot pin stubs 95 extending laterally therefrom. Similarly, second jaw 22 has a pair of pivot pin stubs 97 extending laterally therefrom. As best seen in FIGS. 3, 15 and 18, the pivot pin stubs are received in lateral holes 99 defined through forward extending tabs 101 and 103 defined on the forward end of clip magazine 58. Thus, the jaws 20 and 22 are mounted upon magazine 58 so as to pivot about their pivot pins 95 and 97.

Each of the jaws 20 and 22 also includes a tab 105 or 107, respectively which is constructed for engagement with the outer tube 18. As best seen in FIGS. 3 and 33, the tab 105 of lower jaw 20 is received in a lateral opening 109 in the lower face of tube 18, and the tab 107 of upper jaw 22 is received in a lateral opening 111 defined in the upper face of tube 18. Thus, as outer tube 18 is reciprocated back and forth relative to magazine 58, it pushes and pulls on the tabs 105 and 107 thus causing the jaws 20 and 22 to pivot about their pin stubs 95 and 97 between an open position as shown in FIG. 3 and a closed position as shown in FIG. 5.

The jaws 20 and 22 have windows 113 and 115 defined therein on diametrically opposite sides of the longitudinal axis of outer tube 18. This allows the vessel which is being clamped by the jaws to be viewed through the windows.

It is noted that one particular advantage provided by the present invention is due to the blunt shaped forward ends 208 and 210 of the jaws which are each semispherical in nature so that when the jaws are fully closed, they define a bullet shaped forward probe end 208, 210, as best seen in FIG. 5. This permits the surgeon to close the jaws 20 and 22 and use the apparatus 10 as a probe.

The mechanism which controls the operation of the jaws 20 and 22 and advances the clips 64 through the magazine 58 into the jaws 20 and 22 will now be described.

As best seen in FIG. 3, there is a pusher rod or pusher bar 102 which has a plurality of prongs 104 extending therefrom. Pusher rod 102 may also be referred to as a driver rod 102.

The details of construction of pusher rod 102 are best seen in FIGS. 25–28. The pusher rod 25 includes a plurality of prongs 104 which extend therefrom into engagement with the clips 64 contained in the magazine as seen in FIG. 3. The pusher rod 102 is an elongated flat bar. The pusher rod 102 is slidably received in an open channel 106 (see FIG. 16) defined on the outer surface of magazine 58. Also received in the open channel 106 on the opposite side of pusher rod 102 is a flat strip of resilient foam material 93 which serves as a spring to resiliently hold the prongs 104 in engagement with clips 64.

The pusher rod 102 includes first and second slots 108 and 110 defined therethrough near its rearward end 112. The slots 108 and 110 provide a means for connection of the pusher rod 102 to a pusher rod piston 114.

The details of construction of pusher rod piston 114 are best seen in FIG. 29. The piston 114 has a rearward end 116 and a forward end 118. A portion of the pusher rod 114 adjacent forward end 118 has a flat 120 defined thereon which has first and second keys 122 and 124 extending upward therefrom. The keys 122 and 124 are constructed to be received in the slots 108 and 110 respectively of pusher rod 102.

The rear portion of pusher rod piston 114 has a ledge 123 defined thereon for engagement with take up spring 125 seen in FIG. 3. The rear end 116 of pusher rod piston 114 has a knob 127 thereon which is received through a keyhole shaped opening 193 in actuator lever 184.

The pusher rod piston 114 has an intermediate enlarged diameter portion 126.

As seen in FIG. 32, the intermediate outer tube piston 38 has a bore 132 defined in its rearward end 134. As seen in FIG. 3, the pusher rod piston 114 is slidably received within the bore 132 of intermediate outer tube piston 38.

As previously noted, the barrel 14 has a bore 24 defined in its forward end 26. The barrel 14 further includes first, second and third counterbores 146, 148, and 150, respectively.

Third counterbore 150 is closely received about the cylindrical forward extending projection 13 of handle 12.

The larger diameter forward portion 48 of intermediate outer tube piston 38 is slidably received in the second counter bore 148. An intermediate piston return spring 152 is disposed between the forward end of intermediate piston 38 and a step 154 defined between bore 24 and first counterbore 146. Spring 152 can also be described as a jaw return spring for aiding in opening the jaws.

The magazine 58 has a transverse pin bore 156 defined therethrough near its rear end 158 as best seen in FIG. 17.

As seen in FIG. 3, an anchor pin 160 extends through the pin bore 156 of magazine 58 and into the barrel 14 to anchor the position of magazine 58 relative to barrel 14.

As seen in FIGS. 32 and 39, the intermediate outer tube piston 38 has first and second longitudinal slots 50 and 52 defined therein through which the anchor pin 160 is received. The slots 50 and 52 allow the intermediate outer tube piston 38 to slide longitudinally over the rear end 158 of magazine 58 and over the anchor pin 160.

The smaller diameter rearward portion 46 of intermediate outer tube piston 38 is slidably received within a bore 162 of a primary outer tube piston 164. The primary outer tube piston 164 may also be referred to as a collar 164.

The primary outer tube piston 164 is best shown in FIG. 30. It includes a generally cylindrical forward portion 166 having a forward end 168. Flats such as 170 are formed on the two diametrically opposed sides of forward portion 166. Integrally formed arms 172 and 174 extend rearwardly from the forward portion 166 and are spaced apart in a yoke-like fashion. The rear end 176 of forward portion 166 has a slot 178 formed vertically therethrough.

A safety spring 180 is concentrically received about the smaller diameter rearward portion 46 of intermediate outer tube piston 38 and is received between the forward end 168 of primary outer tube piston 164 and a rearward facing annular face 182 defined on the enlarged portion 48 of intermediate outer tube piston 38. Safety spring 180 is a very stiff spring which in normal operation is relatively non-flexing. The purpose of safety spring 180 is to prevent deformation of the jaws if an unyielding object is trapped between the jaws preventing the jaws from closing, and it supplies added resistance to indicate the jaws are closed and the clips are advanced.

The arms 172 and 174 of the primary outer tube piston 164 extend downwardly and rearwardly into engagement with an actuator or actuator lever 184, and that relationship will be further described below. The actuator lever 184 is pivotally mounted within the housing 12 on pivot pin 186.

The trigger 16 is pivotally mounted within housing 12 on a second pivot pin 188.

The details of construction of the actuator lever 184 are best seen in FIG. 31. It is noted that in FIG. 31, the actuator lever 184 has been rotated 180° about a vertical axis as compared to its position in FIGS. 1 and 3. A transverse pin bore 189 receives the pivot pin 186.

A lower end 190 of actuator lever 184 engages a rear edge 194 of trigger 16 as best seen in FIG. 2.

As the trigger 16 is squeezed to pull it back in to the housing 12, it causes actuator lever 184 to pivot in a clockwise direction as seen in FIG. 2 about the pivot pin 186. A return spring 187 biases lever 184 and trigger 16 back toward their original position. The return spring 187 is shown as a compression spring located behind actuator 184. The return spring 187 could be replaced with a torsion spring (not shown) positioned around post 186.

As best seen in FIG. 31, the actuator lever 184 has a pair of laterally extending pins 196 on either side thereof. The pins 196 engage rearwardmost camming surfaces 198 and 200 defined on the rear ends of arms 172 and 174 of primary outer tube piston 164. Thus, as the trigger 16 is squeezed, and actuator lever 184 pivots clockwise, the lateral pins 196 bearing on camming surfaces 198 and 200 cause the primary outer tube piston 164 to slide forward.

The actuator lever 184 has an upper end 191 which has an opening 193 defined therethrough. The rear end 116 of pusher rod piston 114 is received through opening 184.

It is noted that the primary outer tube piston 164 has a generally cylindrical outer surface 166 which is slidably received within a bore 202 of the cylindrical forward extending handle projection 13.

Description of the Operation of the Apparatus

Upon squeezing of trigger 16, as the actuator lever 184 begins to pivot clockwise, its lateral pins 196, which are in engagement with the camming surfaces 198 and 200 defined on the rear ends of the arms 172 and 174 of primary outer tube piston 164, will push the primary outer tube piston 164 forward relative to housing 12. The forward end 168 of primary outer tube piston 164 pushes safety spring 180, which with essentially no compression pushes against shoulder 182 of intermediate outer tube piston 38 to move piston 38 forward.

It will be recalled that the outer tube 18 is firmly engaged by intermediate piston 38, so the outer tube 18 will immediately begin to slide forward out of the bore 24 of barrel 14 as the trigger 16 is squeezed.

As the outer tube 18 slides forward over the magazine 58 which is fixedly attached to the barrel 14, it will cause the jaws 20 and 22 to pivot inwardly toward each other.

It will be appreciated that only a very small sliding motion of the outer tube 18 relative to the clip magazine 58 is required to pivot the jaws 20 and 22 between their open and closed positions.

Also as the actuator lever 184 pivots clockwise from the initial position of FIG. 2 the lever 184 pushes against take-up spring 125 and ledge 123 to push the pusher rod piston 114 forward within the bore 132 of intermediate outer tube piston 38. As the pusher rod piston 114 slides forward, it also moves the pusher rod 102, which is attached to piston 114, forward within the clip magazine 58. Depending upon the frictional resistance to movement of clips 64 in the magazine 58, there will be some compression of take up spring 125.

It is noted that when trigger 16 is squeezed and actuator lever 184 begins to pivot, force is immediately simultaneously applied to begin closing the jaws and to begin pushing the clips. There is a slight delay in the beginning of movement of the clips due to the compression of spring 125.

As seen in FIG. 3, the pusher rod 102 includes a plurality of prongs 104 which individually engage the clips 64B, 64C, etc. Forwardmost clip 64A is not engaged by push rod 102, but instead abuts the next clip 64B.

Preferably the clips 64B, 64C, 64D, etc., have slight spacings therebetween and do not abut each other. If any of the clips do touch, they only touch slightly, and they do not transfer the pushing force from one clip to another. Instead, if the clips touch slightly, they may move slightly out of alignment with each other. In any event the clips 64B, 64C, 64D are separately engaged by separated prongs 104, and are separately but simultaneously advanced through magazine 58 by the advancing motion of push rod 102.

The forwardmost clip 64A is pushed out of magazine 58 into jaws 20 and 22 by the next adjacent clip 64B. As forwardmost clip 64A is pushed forward, the wire loops 72 and 74 will come into registry with releasing openings 96 and 98 thus allowing the support member 66 and clamping arm 68 of the clip to snap shut toward each other thus clamping the lumen 100 therebetween as the clip 64A is released from the jaws 20 and 22.

After the trigger 16 has been squeezed to close jaws 20 and 22 and advance a clip 64A into the jaws where it is released, subsequent release of trigger 16 will cause it to pivot forward due to spring 187. This will pull back the push rod 102. The column of clips 64 will stay in place within magazine 58 due to the gripping of the magazine ledges 61 and 63 by the clips 64. The prongs 104 will slip back past the clips and engage the next rearward clip on the next squeeze of trigger 16. The ability of the prongs 104 to slip back past the clips 64 is aided by the lateral movement allowed by flexible strip 93 which backs up the push bar 102.

Methods of Ligating a Lumen

As previously noted, the apparatus 10 is especially constructed for use in laparoscopic surgery wherein the apparatus 10 must be inserted through as small an opening as possible in the patient's body.

U.S. Pat. No. 5,593,414, assigned to the assignee of the present invention and incorporated herein by reference, discloses a technology which allows a spring clip to be inserted into the surgical field in the closed state, opened over a vessel, the diameter of which has been reduced or preclamped by the tool, and then closed over the preclamped vessel. That method allows an entry wound to vessel diameter of 1.0 or smaller. Thus, a 5 mm vessel can be ligated through a 5 mm diameter trocar. One aspect of the present invention is the provision of improved preclamping apparatus and methods. Utilizing the apparatus disclosed in U.S. Pat. No. 5,593,414, a vessel is first preclamped at one point along its length, and then the spring clip is applied over the vessel adjacent the point of preclamping. This technique is improved by the present invention in the following manner.

It will be appreciated in reference to FIGS. 19 and 22, that the bottom jaw 20 may be described as being bifurcated to include first and second spaced jaw sides 214 and 216. Similarly, the upper jaw 22 may be described as being bifurcated to include first and second spaced jaw sides 218 and 220.

When the jaws 20 and 22 are closed together, the first jaw sides 214 and 218 clamp the lumen 100 at one point along its length, and the second jaw sides 216 and 220 clamp the lumen 100 at a second point along its length. Then, when the clip 64A is released, the support member 66 and clamping arm 68 clamp the lumen at a third point along its length located between the first and second points.

The closing motion of jaws 20 and 22 may be described as preclamping the lumen 100 by movement of clamping surfaces 214, 216, 218 and 220 in planes substantially perpendicular to a longitudinal axis 222 (see FIG. 37) of the lumen 100.

It is noted that the step of preclamping the lumen 100 between the jaws 20 and 22 typically occurs prior to the step of pushing the spring clip 64A from the magazine 58 into the jaws 20 and 22. As the spring clip 64A is moved into the jaws 20 and 22, it subsequently is released from those jaws when the wire loops move into registry with the releasing openings 96 and 98.

It is also noted that the methods of operating the apparatus 10 includes steps of loading in a plurality of spring clips 64 in the magazine 58 such that the wire loops 72 and 74 are received within the channels 60 and 62 with the clips thus held in an open position. Then, each time that the trigger 16 is compressed, each of the clips 64 is advanced forward in the magazine 58. The clips 64 are arranged in magazine 58 head to tail with a small space between adjacent clips so that the clips are pushed through the magazine 58 by the prongs 104 of the pusher rod 102.

During this procedure rotation of the spring clip 64 is prevented by containing the wire loops, or enlarged ends 72 and 74 thereof in the partially closed channels 60 and 62 of the magazine 58.

Now with reference to FIG. 38, a method will be described for ligating a stub end 224 of a lumen 100. It will be appreciated by those skilled in the art, that sometimes instead of placing the clip 64 transversely across the length of the lumen 100 as illustrated in FIGS. 36 and 37, it will be desirable to approach a stub end 224 of the lumen 100 head on. With all prior art clip designs this can be very difficult.

This can be accomplished with the clip 64 of the present invention owing to the wire loops 72 and 74 providing transversely extending clamping surfaces 226 and 228 (see FIG. 8) which are the forward portions of loops 72 and 74 extending transversely to the length of the clip 64.

Figure 38:
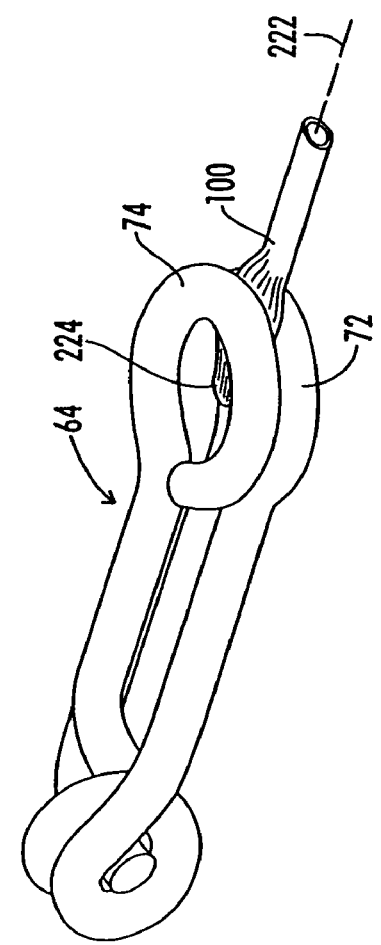
FIG. 38 is a perspective view showing the clip of FIGS. 8–12 being used to ligate a stub end of a lumen.

With reference to FIG. 38, when clamping a stub end 224 of the lumen 100 the clip 64 will generally be oriented with its length at an angle of less than 45° to a length or centerline 222 of the lumen 100.

The bullet shaped forward ends 208 and 210 of jaws 20 and 22 are opened and then placed over the stub end 224. Then, the jaws 20 and 22 are closed together by squeezing the trigger 16 so as to preclamp the lumen 100 at a point spaced a distance from its stub end 224. Jaws 20 and 22 have transverse preclamping surfaces 230 and 232, respectively, defined thereon.

As the trigger is squeezed the forwardmost clip 64 is advanced into the jaws 20 and 22 in a lengthwise direction until the wire loops 72 and 74 are in registry with the releasing openings 96 and 98, which may be described as a position where the stub end 224 of the lumen 100 is located between the two transversely extending clamping surfaces 226 and 228. Then as the wire loops 72 and 74 move into registry with the releasing openings 96 and 98, the clip 64A is released and the wire loops 72 and 74 move toward each other thus clamping the stub end 24 of the lumen 100 between the two transversely extending clamping surfaces 226 and 228 as seen in FIG. 38.

Thus it is seen that the apparatus and methods disclosed readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

We claim:

1. A surgical ligation clip for ligating a fluid carrying structure, said clip comprising:
    a mid-longitudinal axis, a distal end, a proximal end opposite said distal end, and a length between said distal and proximal ends;
    an upper support member extending between said distal and proximal ends;
    a lower support member extending between said distal and proximal ends, said lower support member being opposite said upper support member in a vertical plane parallel to the mid-longitudinal axis; and
    a connector at said proximal end of said clip, said connector joining said upper and lower support members, each of said upper and lower support members including an enlarged section proximate said distal end, each of said enlarged sections having a clamping surface adapted to clamp the fluid carrying structure therebetween, said enlarged section including a central axis generally transverse to said clamping surface, said enlarged section having an exterior surface forming an arc extending more than 180 degrees around the central axis in a plane generally transverse to the central axis.

2. The clip of claim 1, wherein said exterior surface includes two opposed portions that form an arc of a circle in a plane generally transverse to the central axis.

3. The clip of claim 1, wherein said clip is formed of a single piece of wire and has a first free end terminating at said connector and a second free end terminating at one of said enlarged sections.

4. The clip of claim 1, wherein each of said enlarged sections have a clamping surface adapted to clamp the fluid carrying structure therebetween, said clamping surfaces having a maximum separation distance therebetween of 0.75 mm in an open and undeployed position.

5. The cup of claim 1, wherein said connector is adapted to bias said upper and lower support members toward one another into a closed position.

6. The cup of claim 1, wherein said connector includes a coil spring.

7. The clip of claim 1, wherein said connector is adapted to apply a force to said upper and lower support members to bias said upper and lower support members toward one another into a closed position, the force being greater than that needed to move said upper and lower support members into contact with one another.

8. The clip of claim 1, wherein said connector includes a pre-load force between said upper and lower support members of at least 100 grams of force.

9. The clip of claim 1, wherein said clip has a maximum dimension of 5 mm transverse to the mid-longitudinal axis.

10. The clip of claim 1, in combination with a clip applier for applying said clip to the fluid carrying structure.

11. The clip of claim 10, wherein said clip applier includes a magazine adapted to hold a plurality of clips.

12. The clip of claim 1, wherein the fluid carrying structure is a vessel, at least one of said upper and lower support members having a surface configured to enhance gripping of the vessel.

* * * * *

UNITED STATES PATENT AND TRADEMARK OFFICE
CERTIFICATE OF CORRECTION

PATENT NO.         : 7,207,997 B2  
APPLICATION NO. : 10/721681  
DATED                 : April 24, 2007  
INVENTOR(S)       : John I. Shipp et al.

It is certified that error appears in the above-identified patent and that said Letters Patent is hereby corrected as shown below:

<u>Title Page 3, Column 2</u>: item 56  
Line 19: change "WO 88/0148" to -- WO 88/1487 --.

<u>Column 14, lines 26 and 29</u>:  
Change "cup" to -- clip --.

Signed and Sealed this

Twenty-sixth Day of June, 2007

JON W. DUDAS  
*Director of the United States Patent and Trademark Office*